United States Patent
Semlitsch

[19]

[11] Patent Number: 6,126,695
[45] Date of Patent: Oct. 3, 2000

[54] ARTIFICIAL JOINT, PARTICULARLY AN ARTIFICIAL HIP JOINT

[75] Inventor: Manfred Semlitsch, Winterthur, Switzerland

[73] Assignee: Sulzer Orthopaedie AG, Baar, Switzerland

[21] Appl. No.: 09/155,671

[22] PCT Filed: Mar. 6, 1997

[86] PCT No.: PCT/CH97/00090

§ 371 Date: Oct. 1, 1998

§ 102(e) Date: Oct. 1, 1998

[87] PCT Pub. No.: WO97/38650

PCT Pub. Date: Oct. 23, 1997

[30] Foreign Application Priority Data

Apr. 12, 1996 [EP] European Pat. Off. ............. 96810225

[51] Int. Cl.[7] .......................................... A61F 2/32
[52] U.S. Cl. .................... 623/22.15; 623/18.11; 623/23.4
[58] Field of Search ................. 623/18, 22, 23, 623/18.11, 22.15, 23.4

[56] References Cited

FOREIGN PATENT DOCUMENTS

| 0 226 762 A1 | 7/1987 | European Pat. Off. . |
| 0 554 214 A1 | 8/1993 | European Pat. Off. . |
| 0 578 322 A3 | 1/1994 | European Pat. Off. . |
| 0 648 478 A3 | 4/1995 | European Pat. Off. . |
| WO 95/23566 | 9/1995 | WIPO . |

OTHER PUBLICATIONS

Streicher, R.M., et al., "Investigation of the Tribological Behaviour of Metal–on–Metal Combinations for Artificial Hip Joints" in: *Biomedizinische Technik* 35 (1990) May, No. 5, Berlin (in German).

*Primary Examiner*—Michael J. Milano
*Attorney, Agent, or Firm*—Townsend and Townsend and Crew LLP

[57] ABSTRACT

With the invention, a geometry is described which makes it possible to use similar, wear-resistant, metallic materials such as PROTASUL 21 WF for a bearing shell (1) and a joint ball (2) in a spherical bearing without micro-weldings and without excessive wear arising, while other properties such as toughness, stability of shape and elasticity can be exploited for the function. Micro-weldings of the similar metallic materials are largely prevented by a suitable relationship between the average radii $R_m$, $r_m$ of the bearing surfaces A and B as well as of the permissible deviations (12, 13) in shape and of the permissible roughness of the bearing surfaces.

14 Claims, 3 Drawing Sheets

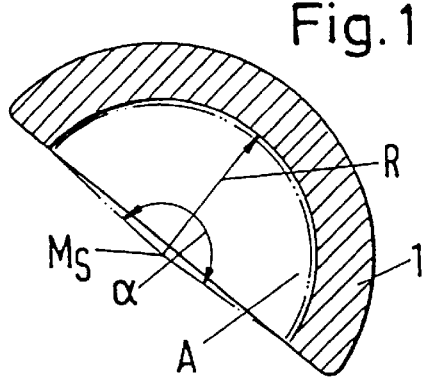
Fig. 1
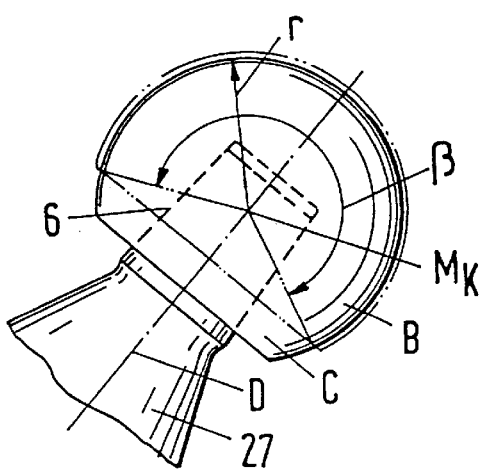 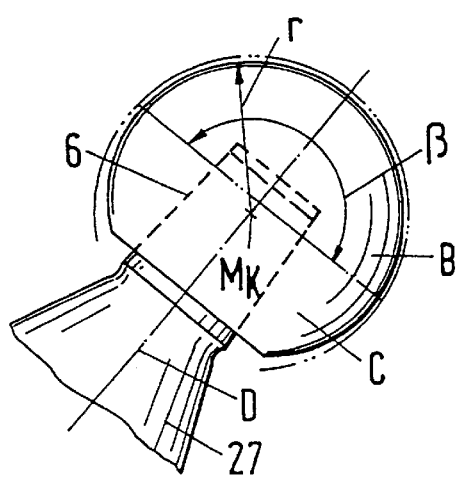
Fig. 2a    Fig. 2b
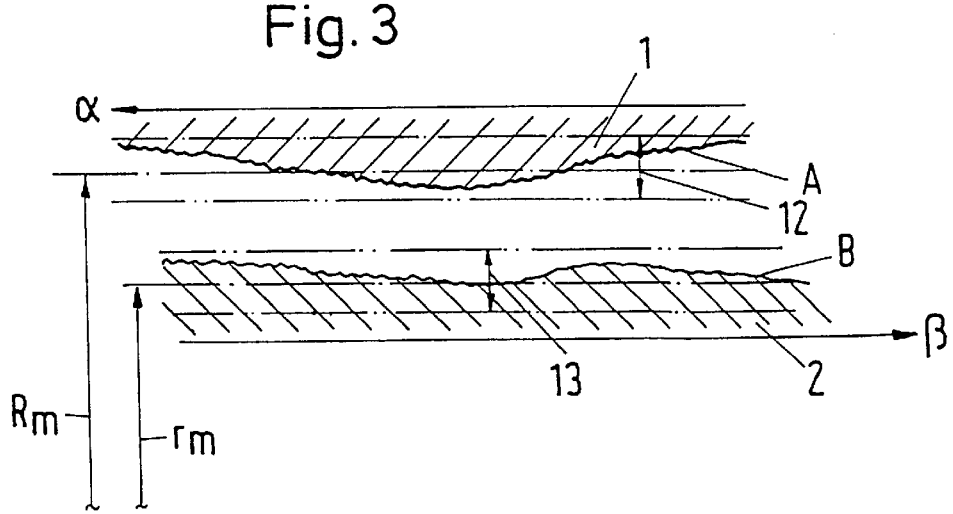
Fig. 3

ARTIFICIAL JOINT, PARTICULARLY AN ARTIFICIAL HIP JOINT

BACKGROUND OF THE INVENTION

The invention relates to an artificial joint, in particular to an artificial hip joint, comprising a bearing shell which has a concave spherical bearing surface A with center $M_S$, and with a joint ball which has a convex spherical bearing surface B with center $M_K$, which as a rule is rotationally symmetrically arranged with respect to a mounting axis D in the direction of the femur neck of an artificial hip joint shaft.

Artificial joints require pairings of the materials of the bearing bodies which move relative to one another which have good emergency running properties. The classical starting point in the combination of materials thus consists in pairing dissimilar partners. Thus relatively soft bearing shells of polyethylene are combined with hard joint heads of metal or ceramics and, in the early days of the artificial hip joints, metallic materials of differing hardness and wear resistance were combined with one another. In spite of all efforts, it was never possible to completely eliminate the wear of the partners with these material combinations. With polyethylene, for instance, an abrasion takes place in the hip joint through which the bearing surface is recessed by approx. 0.2 mm yearly in the direction of the principal force. Even with metallic surfaces wear arises due to point loads and micro-weldings at the surfaces which—once they have begun—very rapidly affect the entire surface of engagement.

SUMMARY OF THE INVENTION

It is an object of the invention to attain a low-wear arrangement. This is satisfied in that the bearing shell and the joint head consist of a wear-resistant metallic material; in that the surface A has an average radius $R_m$ and the surface B has an average radius $r_m$, with their difference amounting to 35 $\mu m < R_m - r_m < 85$ $\mu m$; in that the shape error of the surface A amounts to less than ±7.5 $\mu m$ over an angle $90° < \alpha < 180°$; in that the shape error of the surface B amounts to less than ±2 $\mu m$ over an angle $\beta > 140°$; and in that the joint ball is continued outside the area B by a set-back surface C which has a distance to the center $M_K$ which is less than that of surface B, while the roughness of the surface A corresponds to a value $R_a < 0.08$ $\mu m$ and the roughness of the surface B corresponds to a value $R_a < 0.08$ $\mu m$. By manufacturing, measuring and pairing of bearing surfaces of the same wear-resistant metallic material, a geometry between the bearing surfaces is achieved which, together with the capillary action of the body fluid and the buoyancy in bearing surfaces gliding past one another, largely eliminates micro-weldings and wear. Through the suppression of micro-weldings for identical wear-resistant metallic materials, the positive properties of these materials such as toughness, stability of shape and elasticity can be exploited. Surfaces with a homogeneous structure arise which neither break through due to hardness differences between the surface and base body under high stress nor separate from the base body. At the same time, the surfaces are matched so well to one another that no unallowable surface pressure arises when standing still. Especially suitable materials are cobalt, chromium and nickel alloys such as for instance the material PROTASUL 21 WF of the SULZER AG corporation-in accordance with ISO 5832/4 when manufactured in accordance with a method in which a circular generator for the spherical form likewise rotates, but with its axis of rotation swivelled with respect to the axis of rotation of the workpiece in order to grind, hone and polish a spherical shape until the prespecified tolerances for the diameter, accuracy of shape and surface quality have been attained.

This effect will be still better if the roughness of the surfaces A and B corresponds to a value $R_a < 0.05$ $\mu m$.

Advantageous further developments of the invention relate to releasable connections for inner shells which are known from the use of inner shells of relatively elastic polyethylene. These cannot be adopted by inner shells of substantially tougher metallic materials. The function and the manufacturing requirements speak against this. It is thus sensible to firmly connect the bearing shell at its outer side to an intermediate body of an elastic plastic such as polyethylene, for example, which can itself be removably connected to an outer shell. In particular, even implanted plastic shells can be replaced by the metallic bearing shells if the removable connection of the intermediate body is the same. Likewise, the joint balls at prosthesis shafts which are required due to the requirements on precision can be replaced if the joint balls have a releasable connection, for example if they have a removable cone connection on the shaft. Due to the fact that the joint ball and the bearing shell are replaceably executed, they can be brought all the way to the operating table in sterile packaging. The control of the position of an implanted joint is still performed with manipulation joint balls which do not damage the shell, whereas the precision balls are not inserted until near the end.

Interestingly, it has proved that for a given roughness Ra the errors in shape of the individual parts in a low-wear metal/metal pairing play a greater role than the bandwidth within which the difference of the average radii $R_m - r_m$ may lie. For a ball diameter common in artificial hip joints, for example for a nominal diameter of 28 mm, the difference of the average radii may amount to 35 $\mu m < R_m - r_m < 85$ $\mu m$, which corresponds to a bandwidth of 50 $\mu m$ if absolute production dimensions and not selective pairings are taken as the starting point. On halving this bandwidth, an absolute production precision of 25 $\mu m$ for the average radius $R_m$ or $r_m$ would remain for both parts. These values are large enough to be able to dispense with a selection pairing and thus to be able to pair each ball with each bearing shell. This is however possible only if the precise shape can be controlled. This must be observed very precisely and requires special production methods in order to achieve the required tolerance values. The prespecified values for the diameter, stability of shape and roughness are achieved in that the bearing shell as a workpiece is mounted in the form of a pre-turned shell which is undersize in the area of the bearing surface A with the polar axis of the bearing shell being aligned with the axis of rotation of a machine-tool spindle; or in that the pre-turned joint ball as a workpiece is mounted with its mounting axis D aligned with the axis of rotation of a machine-tool spindle and is oversize in the area of the bearing surface B; and in that during the rotation of the workpiece a circular edge of the front side of a circularly cylindrical abrasion body, which is rotatingly mounted with its cylinder axis along the axis of rotation of a tool spindle, is pressed against the bearing surface A, B of the workpiece while abrasive means are added, with the axis of rotation of the tool spindle intersecting the axis of rotation of the tool spindle and at a deflection angle $\gamma, \delta < 90°$ and with the contact pressure being exerted by advancing the tool spindle in the direction of its axis of rotation.

This arrangement has the advantage that the tool and the workpiece—within the framework of the stiffness of the spindles on which they are mounted—mutually center at the working surfaces. As a result of the movement which occurs during the process a wear arises at the workpiece and at the tool which necessarily leads to the formation of a spherical surface on both pieces. At the tool a narrow circular band of a spherical surface arises at a broken edge at the end face, while spherical surfaces A, B arise at the workpiece for the same spherical form. Due to the fact that each point of the work surface of the tool comes into contact with each point of the worked surface, perfect sections A, B of spherical surfaces arise.

It is advantageous for the production of the bearing surface A of a bearing shell to choose the angle between the axes of rotation of the bearing shell and the tool to lie between 39° and 45° in such a manner that the largest possible limiting angle α for the bearing surface arises, since then the diameter for the generator and a cylinder corresponding to it can be chosen so large that the limiting angle α can increase towards 180° without the cylinder touching the inner edge of the shell. Thus only a guided feed or advance movement in the direction of the axis of rotation of the tool is required in order to achieve a larger limiting angle α. For a limiting angle α which is less than 180° by a considerable amount, it is admittedly possible to choose larger circle diameters for a generator, but on the other hand the generator is then only in contact as an interrupted circle.

In the production of the joint ball it has proved that a bearing surface B with a limiting angle β of about 180° with an accuracy of shape of ±2 μm is already sufficient for the function of the bearing insofar as, on the one hand, all other surface parts at the joint ball stand further back and, on the other hand, the equator of the bearing shell and that of the bearing surface B are aligned approximately parallel to one another in the normally loaded state. The deflection angle γ for a rotating tool with a circularly cylindrical hollow cylinder can be set within larger limits, for example between 60° and 20°, in order to produce a bearing surface B. Since the generating circular ring surface does not reach the center of the bearing surface B even for a limiting angle β of more than 180°, the diameter of the joint ball can be measured across the bearing surface B during the working, for example by means of a probe with diamond studded probe surfaces, in order to extrapolate the remaining working time with sufficient precision.

Apart from polishing a run-in radius at the equator of the bearing surface A of the bearing shell, the other work steps can be performed automatically on a numerically controlled machine-tool for the required precision of the bearing shell and the joint ball.

The low wear on the ball and the bearing shell further opens up the advantage that with the embodiment in accordance with the invention no re-operation is necessary due to deteriorating bearing surfaces. For this reason the joint balls for cemented prosthesis shafts can even be connected in a single piece to the shaft and for directly inserted shafts, e.g. of titanium, can be secured with a permanent connection as long as the operation technique does not prescribe a subsequent attachment of the ball to the implanted shaft for reasons of space. It is in particular worthwhile to employ anatomically matched and firmly anchorable shafts which have an S-shaped shaft form with an ante-version of the proximal neck region and with a shaft end projecting towards the posterior in a curve or a kink, since the date for a further operation is now determined only by the duration of the anchoring.

BRIEF DESCRIPTION OF THE DRAWINGS

FIG. 1 is a longitudinal section through the bearing shell;

FIG. 2a is a section through a joint ball with a limiting angle β>180°;

FIG. 2b is a section through a joint ball with a limiting angle β<180°;

FIG. 3 is an unwound profile graph of a bearing shell and a joint ball which are arranged at a distance of their average radii to one another;

DESCRIPTION OF THE PREFERRED EMBODIMENTS

Figure 4:
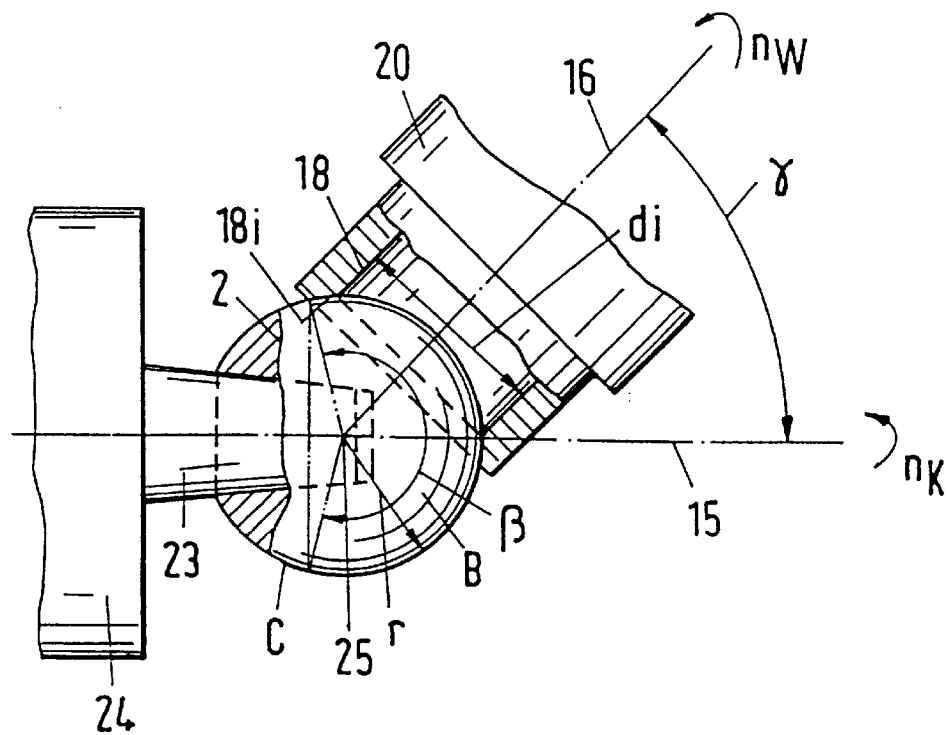
FIG. 4 is a schematic representation of an arrangement of a joint ball and a tool during the production on a machine-tool.

A geometry is described by the figures which enables like, wear-resistant, metallic materials such as PROTASUL 21 WF to be used for the bearing shell 1 and the joint ball 2 in a spherical bearing without micro-welding and excessive wear arising, while other properties such as toughness, form retention and elasticity can be exploited for the function. Micro-welding of the like materials is largely prevented by a suitable relationship between the average radii $R_m$, $r_m$ of the bearing surfaces A and B as well as by the permissible form deviations 12, 13 and by the permissible roughness of the bearing surfaces.

FIG. 1 shows a bearing shell 1 for an artificial hip joint whose spherical bearing surface A extends over an angle α of somewhat less than 180° and has a distance R from a center of the surface. In analogy with this, a joint ball 2 is shown in FIGS. 2a and 2b having a spherical bearing surface B which extends over an angle β>140° and has a distance r from a center $M_K$ of the surface of the joint ball.

Both joint balls in FIGS. 2a and 2b are continued outside the bearing surface B by a quasi-spherical surface C which however has a lesser distance from the center $M_K$ of the bearing surface B than the radius r of the bearing surface B. The lesser distance arises for example by the joint ball already being flattened off or conically formed with respect to the future center $M_K$ in the region C prior to grinding. The joint ball is connected to a prosthesis shaft 27 via a removable conical connection 6. The mounting axis D of the cone coincides with the axis of rotation for the rotationally symmetric bearing surface B so that the bearing surface B always takes on the same position independently of the conical mounting.

FIG. 3 shows a sensed section over the surfaces for the spherical surfaces A and B, both in developed form. Beginning from a non-illustrated common base line the surface A is plotted over an angle α at an average distance of $R_m$ and the surface B is plotted over an angle β at an average distance of $r_m$. Here the magnification perpendicular to the probing direction is shown several powers of ten greater than the magnification in the probing direction. The permissible form error for the surface A of the bearing shell with respect to the average radius $R_m$ lies within a bandwidth of ±7.5 μm and the roughness amounts to $R_a$<0.05 μm. For the surface B of the sphere the permissible form error with respect to the average radius $r_m$ amounts to ±2 μm and the roughness amounts to $R_a$<0.05 μm. If in addition to this combination the difference of the average radii lies within the limits 35 μm<$R_m - r_m$<85 μm and a wear-resistant metal alloy is present as material for the bearing shell 1 and the joint ball 2, which for example has deposits of block carbide as a support surface, then bearing figures are achieved which largely exclude micro-welding and destruction of the surface for normal loads on a hip joint in spite of the similarity of the metal alloys.

The arrangement in FIG. 4 relates to a joint ball 2 which is secured with an inner cone on a mounting pin 23, with the pin 23 belonging to a machine-tool spindle 24 and rotating about its axis of rotation 15 at a speed $n_K$ of 850 rpm for example. A tool spindle 20 deflected by an angle γ of for example 30° rotates about its axis of rotation 16 with a speed of for example 2000 rpm, with the two axes of rotation 15, 16 intersecting at a point of intersection 25 which forms the center for the later finished joint ball 2. A circular hollow cylinder 18 is mounted coaxially in the tool spindle 20 as a machining tool for grinding, honing or polishing and has a circularly broken inner edge 18i which forms a generatrix with an inner diameter di. The hollow cylinder consists of the usual materials for grinding without bound granules such as e.g. metallic oxides or carbides. By addition of a non-illustrated abrasive and by pressing the front side of the hollow cylinder 18 in the direction of the axis of feed and rotation 16 the generating surface 18i and the bearing surface B grind each other to form perfect sections of spherical surfaces, with the radius r of the bearing surface B decreasing very slowly and with the generatrix 18i being enlarged to a circular, spherically arched band. By a corresponding choice of materials the wear at this band can be kept low. The bearing surface B thus arising can be defined by an associated limiting angle β and depends in its magnitude on the deflection angle γ of the tool and on the diameter di of the generatrix. Accordingly, bearing surfaces B with a limiting angle β greater and smaller than 180° are possible, as indicated in FIGS. 2a, 2b. For a limiting angle β>180° as in FIG. 4, the decrease in the radius r during grinding can be determined by a diameter measurement above the point of intersection 25 of the two axes of rotation 15, 16 in order to set the time of discontinuation of the grinding for the finished value of the radius r at an extrapolatable time. Preferable ranges of 20°≦γ≦60° and 1.8 r>di>1.1 r can be specified for the deflection angle γ and for the inner diameter di.

Figure 5:
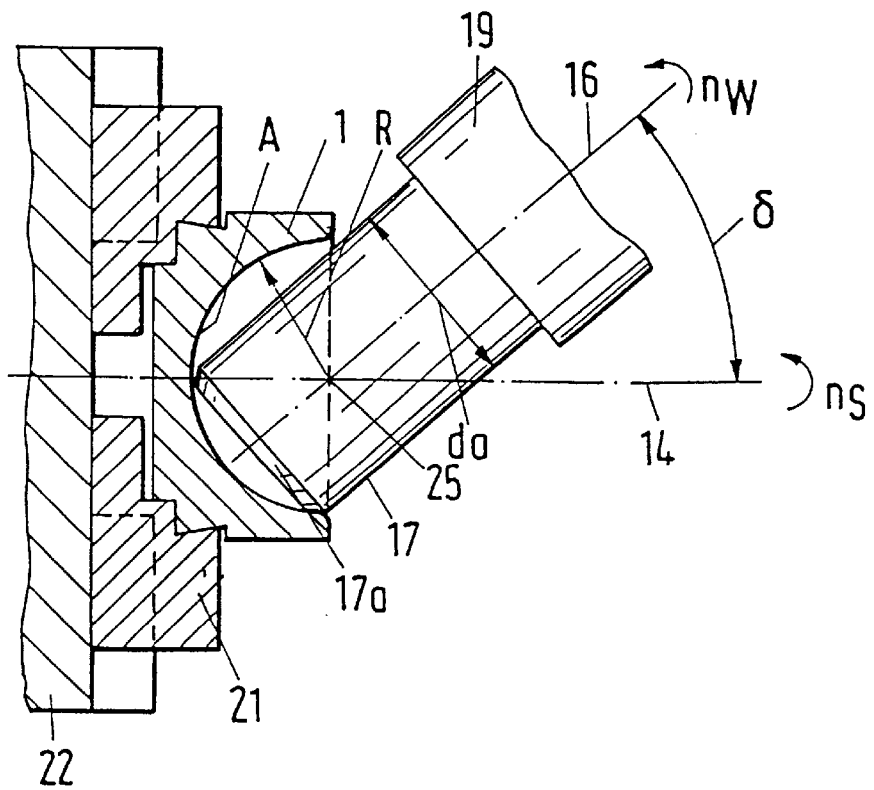
FIG. 5 shows an arrangement of a bearing shell and a tool during the production on a machine-tool.

In the arrangement in accordance with FIG. 5 a bearing shell 1 is mounted in a machine-tool spindle 22 with a mounting chuck 21 in such a manner that the polar axis of the bearing shell 1 and the axis of rotation 14 of the spindle 22 coincide, with the spindle 22 rotating at a speed $n_S$ of for example 850 rpm. A tool spindle 19 is deflected by a deflection angle δ and its axis of rotation 16 intersects the axis of rotation 14 of the workpiece spindle 22 at a point of intersection 25, which corresponds to the center of the later bearing surface A. A circular full cylinder 17 is mounted coaxially into the tool spindle as a tool for grinding without bound granules and rotates at a speed of for example 2050 rpm and forms a circular generator 17a with an outer edge of its end face. By addition of abrasive and adjustment of the generator 17 in the direction of the axis of rotation 16 of the tool, the bearing surface A and the generator are forced to grind one another into perfect sections of spherical surfaces. In order to be able to better manage the value for the radius R, the edge 17 is provisionally trimmed to a spherical form. This has the advantage that the wear on the tool produces only slight changes in the dimensions and that the achievement of a prespecified radius R at the bearing shell 1 is facilitated. A preferential range of 39°<δ<45° results for the deflection angle δ. If the limiting angle α for the bearing surface is not to lie too far below 180° and for example only an advance in the direction of the axis of rotation 16 of the tool is to be performed, then a preferred range of use:

$$1.6R < \frac{d_a}{\cos\delta} < 2.2R.$$

results for the outer diameter $d_a$ of the generator and the deflection angle δ.

The representation in FIG. 3 serves to indicate the theoretical relationships which apply to the dimensional differences of the average radii $R_m$, $r_m$ as well as to the tolerance 12 for the form error of the bearing shell and the tolerance 13 for the form error of the joint ball and to the roughness of the surfaces A, B. In practice the quality of the joint balls 2 can be monitored by roundness measurements using a "Talyround" measuring instrument, while the bearing shells located on a measuring machine are probed at their inner surfaces in various planes by a measurement probe moved radially up to the surface in order to determine an average spherical shape from the measurement points and to interpolate the form deviations. The permissible shape error for a joint ball 2 in the region of the bearing surface B amounts to ±2 μm, whereas a shape error of ±7.5 μm is permissible for the bearing surface A. For both parts the roughness $R_a$ lies below 0.08 μm, preferably below 0.05 μm.

Figure 6:
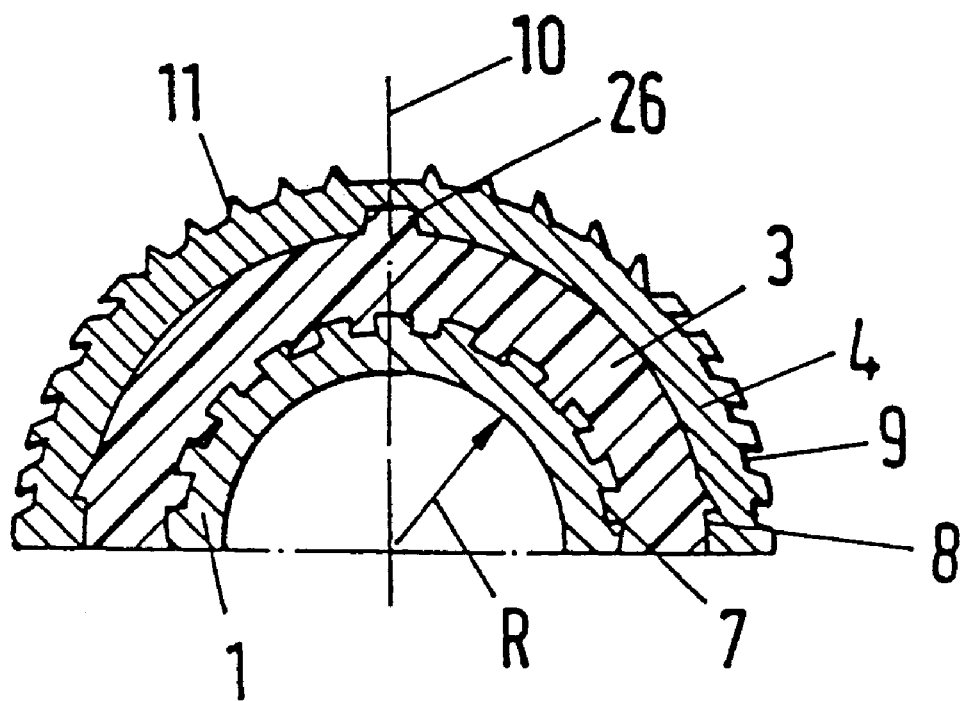
FIG. 6 shows a bearing shell which is firmly connected to an intermediate plastic body which is itself removably secured in an external shell.

The bearing capacity of this nearly wear-free arrangement is so favorable that the radius for the joint ball and for the bearing shell, as indicated in FIG. 6, can be made smaller than that of a usual polyethylene bearing shell. This means that the replacement of the bearing shell and the joint head is also possible for implanted outer shells 4 which have a replaceable polyethylene shell, since the metallic bearing shell 1 can be provided with an intermediate body 3 of polyethylene of sufficient wall strength whose outer dimensions correspond to those of the original polyethylene shell. The intermediate body 3 firmly connected to the bearing shell 1 via a connection 7 can have a somewhat smaller wall thickness than the original polyethylene bearing shell. This has the advantage that implanted replaceable polyethylene shells can be replaced by a corresponding metallic shell with an intermediate body of polyethylene. The outer shell 4 in FIG. 6 has a toothed arrangement 9 which points in the direction of the equator extending up to two-thirds of the height of its outer side, while spikes 11 which are directed parallel to the polar axis are placed on the upper third of the outer side. An outer shell of this kind can be hammered into a bone cavity prepared with undersize. In the process the spikes 11 can penetrate into a non-illustrated bone bed, while the downwardly directed toothing can glide past the bone bed under prestress and, in a final position, the tooth tips prevent backwards sliding in order to achieve a sufficient primary anchoring.

What is claimed is:

1. Artificial joint, comprising a bearing shell which has a concave spherical surface A with a center $M_s$, and a joint ball which has a convex spherical surface B with a center $M_K$, which is rotationally symmetrically arranged with respect to a mounting axis D in the direction of a neck of an artificial joint shaft connected with the joint ball, the bearing shell and the joint ball comprising a wear-resistant metallic material; the surface A having an average radius $R_m$ and the surface B having an average radius $r_m$, with their difference amounting to 35 μm<$R_M$−$r_m$<85 μm; wherein the shape error of the surface A amounts to less than ±7.5 μm over an angle 90°>α<180°; wherein the shape error of the surface B amounts to less than ±2 μm over an angle β>140°; wherein the joint ball is continued outside the area B by a set-back surface C which has a distance to the center $M_K$ which is less than that of surface B, while a roughness of the surface A corresponds to a value $R_a<0.08$ μm and a roughness of the surface B corresponds to a value $R_a<0.08$ μm.

2. Artificial joint in accordance with claim 1 wherein the roughness of the surface A corresponds to a value $R_a<0.05$ μm and the roughness of surface B corresponds to a value $R_a<0.05$ μm.

3. Artificial joint in accordance with claim 1 wherein the bearing shell is securely connected at its outer side to an intermediate body via a connection, with the intermediate body being releasably connected to an outer shell.

4. Artificial joint in accordance with claim 3 wherein the material of the intermediate body is more elastic than the material of the metallic bearing shell by a factor of more than 10.

5. Artificial joint in accordance with claim 1 in wherein the joint ball can be connected to the shaft via a releasable cone connection in the direction of the mounting axis D in order to obtain a uniformly acting partial spherical surface B independently of the connection.

6. Method for the manufacture of an artificial joint including a bearing shell which has a concave spherical surface A with a center $M_s$, and a joint ball which has a convex spherical surface B with a center $M_K$, which is rotationally symmetrically arranged with respect to a mounting axis D in the direction of a neck of an artificial joint shaft connected with the joint ball, the bearing shell and the joint ball comprising a wear-resistant metallic material; the surface A having an average radius $R_m$ and the surface B having an average radius $r_m$, with their difference amounting to 35 μm$<R_m-r_m<$85 μm; wherein the shape error of the surface A amounts to less than ±7.5 μm over an angle $90°<\alpha<180°$; wherein the shape error of the surface B amounts to less than ±2 μm over an angle $\beta>140°$; and wherein the joint ball is continued outside the area B by a set-back surface C which has a distance to the center $M_K$ which is less than that of surface B, while a roughness of the surface A corresponds to a value $R_a<0.08$ μm and a roughness of the surface B corresponds to a value $R_a<0.08$ μm, the method comprising the steps of mounting the bearing shell as a workpiece in the form of a pre-turned shell which is undersize in the area of the bearing surface A with a polar axis of the bearing shell being aligned with an axis of rotation of a machine-tool spindle; or mounting the pre-turned joint ball as a workpiece with its mounting axis D aligned with an axis of rotation of a machine-tool spindle and is oversize in the area of the bearing surface B; pressing during the rotation of the workpiece a circular edge of the front side of a circularly cylindrical abrasion body, which is rotatingly mounted with its cylinder axis along an axis of rotation of a tool spindle, against the bearing surface of the workpiece while adding abrasive means, the axis of rotation of the tool spindle intersecting the axis of rotation of the workpiece spindle at a point of intersection and at a deflection angle $(\gamma,\delta)<90°$; and exerting contact pressure by advancing the tool spindle in the direction of its axis of rotation.

7. Method in accordance with claim 6 wherein the angle ($\delta$) between the axis of rotation of the tool spindle and the axis of rotation of the machine-tool spindle amounts to between 45° and 39°; and including choosing the outer diameter $d_a$ of a circular edge in such a manner that:

$$1.6 R < \frac{d_a}{\cos\delta} < 2.2 R \text{ is adhered to.}$$

8. Method in accordance with claim 6 wherein the angle ($\delta$) between the axis of rotation of the tool spindle and the axis of rotation of a joint ball spindle amounts to between 20° and 60°; and wherein inner diameter $d_i$ of a circular edge satisfies the condition that 1.8 r>$d_i$>1.1 r.

9. Method in accordance with claim 6 wherein the workpiece as a bearing shell rotates with a speed of rotation $n_s$, or wherein the workpiece as a joint ball rotates with a speed of rotation $n_K$, while the tool has a speed of rotation $n_w$ which is approximately twice that of the workpiece.

10. Method in accordance with claim 6 including using the method for grinding, honing or polishing.

11. Method in accordance with claim 8 including performing a diameter measurement during the machining of the joint ball over the surface B across the center $M_K$ in order to establish a remaining time for the machining to a pre-specified diameter by means of a control system as a result of stored values for the abrasive performance.

12. Artificial hip joint in accordance with claim 1 wherein the shaft has an S-shaped, anatomically adapted shaft form with an ante-version in a proximal neck region and with a shaft end projecting towards the posterior in a curve or in a bend in order to attain as long an anchoring duration as possible.

13. An artificial joint in accordance with claim 1 wherein the artificial joint comprises a hip joint.

14. A method in accordance with claim 9 wherein the speed of rotation $n_w$ has a value other than an integral multiple of the speed of rotation of the workpiece.

* * * * *